United States Patent
Zein et al.

(10) Patent No.: US 11,957,351 B2
(45) Date of Patent: Apr. 16, 2024

(54) TISSUE LIGATION SYSTEMS AND METHODS OF LIGATING TISSUE

(71) Applicant: THE CLEVELAND CLINIC FOUNDATION, Cleveland, OH (US)

(72) Inventors: Nizar Zein, Highland Heights, OH (US); Shengqiang Gao, Beachwood, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 122 days.

(21) Appl. No.: 17/522,709

(22) Filed: Nov. 9, 2021

(65) Prior Publication Data
US 2022/0142648 A1 May 12, 2022

Related U.S. Application Data

(60) Provisional application No. 63/111,116, filed on Nov. 9, 2020.

(51) Int. Cl.
*A61B 17/12* (2006.01)
*A61B 17/00* (2006.01)
*A61B 17/29* (2006.01)

(52) U.S. Cl.
CPC .... *A61B 17/12013* (2013.01); *A61B 17/2909* (2013.01); *A61B 2017/00778* (2013.01);
(Continued)

(58) Field of Classification Search
CPC .......... A61B 17/12013; A61B 17/2909; A61B 2017/00778; A61B 2017/00818;
(Continued)

(56) References Cited

U.S. PATENT DOCUMENTS 5,897,487 A    4/1999   Ouchi
6,152,936 A *  11/2000  Christy ............ A61B 17/12013
                                                606/139
(Continued)

FOREIGN PATENT DOCUMENTS

JP        H10286224 A      10/1998
WO    WO-2006119762 A1 *  11/2006   ....... A61B 17/12013
(Continued)

OTHER PUBLICATIONS

PCT International Search Report and Written Opinion for corresponding International Application Serial No. PCT/US2018/027441, dated Aug. 31, 2018, pp. 1-22.

*Primary Examiner* — Erich G Herbermann
*Assistant Examiner* — Nasheha Baset
(74) *Attorney, Agent, or Firm* — TAROLLI, SUNDHEIM, COVELL & TUMMINO L.L.P.

(57) ABSTRACT

Tissue ligation systems and methods are provides to mechanically strangulate abnormal or undesirable tissue. Tissue ligation systems include a multi-lumen catheter having an outer diameter smaller than the inner diameter of a standard endoscope channel such that the catheter can be inserted into the endoscope. Tissue ligation systems also include a ligation apparatus with an expandable hood disposed at the distal end of the catheter. A suture extends through a lumen of the catheter and has a distal loop portion that can strangulate tissue.

12 Claims, 18 Drawing Sheets

(52) U.S. Cl.
CPC .............. *A61B 2017/00818* (2013.01); *A61B 2017/291* (2013.01)

(58) Field of Classification Search
CPC .... A61B 2017/291; A61B 2017/00561; A61B 2017/306; A61B 2018/141; A61B 17/282; A61B 17/12; A61B 17/12009; A61B 17/122; A61B 17/132; A61B 17/128; A61B 17/12022; A61B 17/1285
See application file for complete search history.

(56) References Cited

U.S. PATENT DOCUMENTS

| | | | |
|---|---|---|---|
| 2006/0253129 A1* | 11/2006 | Liddicoat | A61B 17/00234 606/139 |
| 2009/0093809 A1 | 4/2009 | Anderson et al. | |
| 2013/0225934 A1* | 8/2013 | Raybin | A61B 1/018 606/170 |
| 2013/0325025 A1* | 12/2013 | Hathaway | A61B 17/00234 606/114 |
| 2016/0249932 A1* | 9/2016 | Rogers | A61B 17/0469 606/144 |

FOREIGN PATENT DOCUMENTS

| | | | | |
|---|---|---|---|---|
| WO | 2013/169856 A1 | 11/2013 | | |
| WO | WO-2013169856 A1 * | 11/2013 | ......... | A61B 17/0469 |
| WO | 2018/057963 A1 | 3/2018 | | |

* cited by examiner

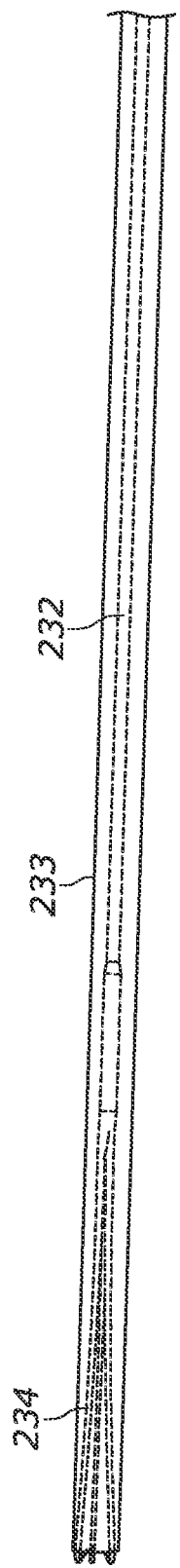
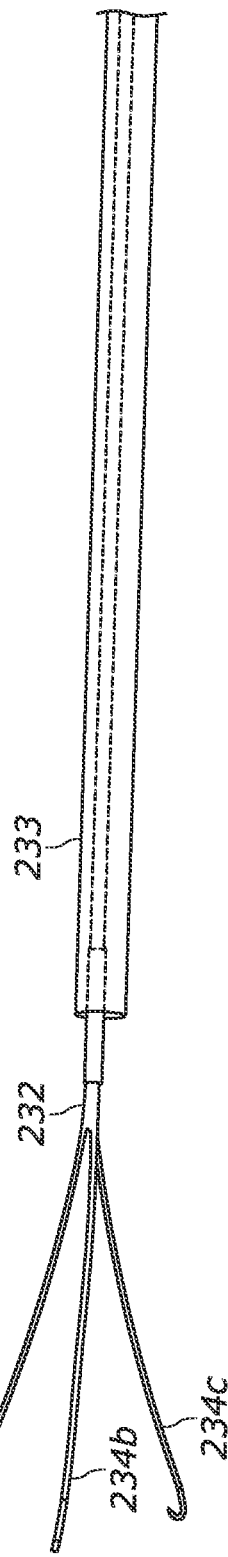
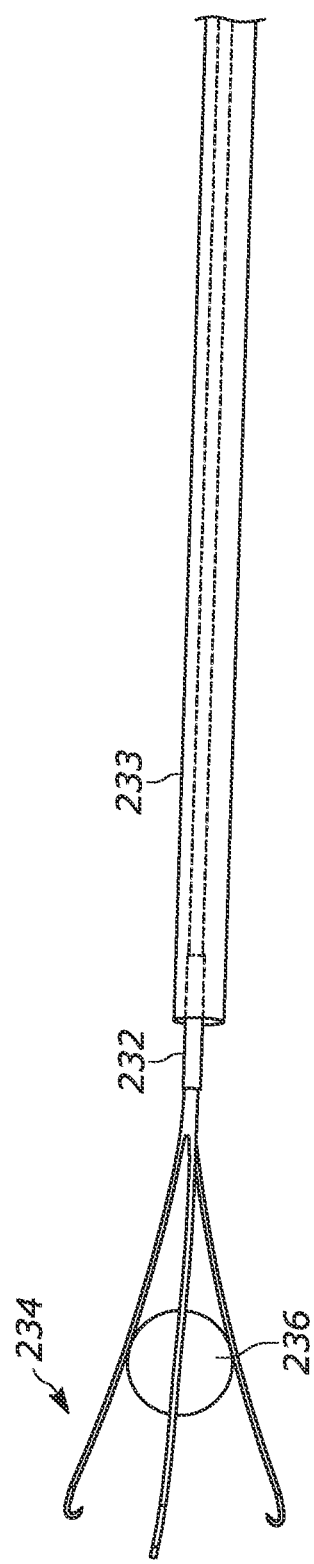
FIG. 16
FIG. 17
FIG. 18

TISSUE LIGATION SYSTEMS AND METHODS OF LIGATING TISSUE

CROSS-REFERENCE TO RELATED APPLICATIONS

The present application claims priority to U.S. Provisional Application No. 63/111,116, filed on Nov. 9, 2020, the contents of which are incorporated by reference in their entirety.

TECHNICAL FIELD

The present disclosure relates to systems and methods of ligating and strangulating tissue in a patient.

BACKGROUND

Varices are abnormally dilated vessels most commonly detected in the distal esophagus or proximal stomach. Despite advances in therapy over the last decade, variceal hemorrhage is associated with a mortality of at least 20% at 6 weeks. Endoscopic therapies for varices aim to reduce variceal wall tension by obliterating the varix. The two principal methods for treating varices are endoscopic sclerotherapy (EST) and endoscopic band ligation (EBL). EBL obliterates varices by causing mechanical strangulation with elastic bands. In general, an endoscope loaded with an elastic band is inserted into the varix to be banded. The varix is suctioned into a plastic hollow cylinder or cap attached to the endoscope tip. The elastic band is slipped over the tissue, causing necrosis, ulceration and eventual sloughing of the varix.

Esophageal varices are often associated with portal hypertension. Portal hypertension is an increase in the pressure within the portal vein. The increase in pressure is generally caused by a blockage in the blood flow through the liver. Increased pressure in the portal vein causes large varices to develop across the esophagus and stomach to bypass the blockage.

The most common cause of portal hypertension is cirrhosis. It is estimated that there are over 630,000 individuals with liver cirrhosis in the United States. Additionally, at least 30,000 new cases of cirrhosis are diagnosed annually. Nearly 90% of patients with cirrhosis will develop esophageal varices during their lifetime and 30% of patients will have an episode of variceal bleeding. EBL is recommended for the prevention of bleeding particularly in those patients with medium or large size varices.

SUMMARY

Systems and methods for ligating tissue are provided herein. In an aspect, a tissue ligation system is provided that includes a multi-lumen catheter, a ligation apparatus, and a retractable handle. The multi-lumen catheter can have a distal end, a proximal end, and a catheter body extending longitudinally therebetween. The multi-lumen catheter can have an outer diameter smaller than the inner diameter of a biopsy channel of an endoscope. The multi-lumen catheter can include a vacuum lumen extending longitudinally through the catheter body, at least a suture lumen extending longitudinally through the catheter body, and an inflation lumen extending longitudinally between the proximal end and the distal end of the catheter. The ligation apparatus can comprise an inflatable member located at the distal end of the catheter and in communication with the inflation lumen of the catheter. The ligation apparatus can also include an expandable hood located at the distal end of the catheter and disposed about the inflatable member. The expandable hood can be expandable via inflation of the inflation member. The ligation apparatus can further comprise a suture extending through the suture lumen and having a distal portion and a proximal portion. The distal portion can comprise a distal loop and a collar disposed about the suture. The collar can permit movement of the suture in one direction and can resist movement of the suture in an opposite direction. The proximal portion of the suture can be releasably coupled to a wire. The retractable handle can be located at the proximal end of the catheter and can be operably coupled to the wire.

In another aspect, a method of ligating tissue is provided. The method can comprise inserting an endoscope having a channel into the patient and inserting the multi-lumen catheter and ligation apparatus as described above into the channel. The method can further include positioning the expandable hood and distal loop of the suture adjacent to the tissue to be ligated, expanding the expandable hood, and suctioning tissue into the hood. The method can further include retracting the handle proximally to cinch and secure the tissue in the distal loop of the suture. The method can further comprise mechanically releasing the wire from the suture, deflating the inflatable member, and retrieving the catheter, the inflatable member and the expandable hood from the patient.

In another aspect, a tissue ligation system is provided comprising a catheter having a distal end, a proximal end, and a lumen extending longitudinally therethrough. The catheter has an outer diameter smaller than the inner diameter of a biopsy channel of an endoscope. The tissue ligation system includes a cage comprising a plurality of circumferentially disposed struts and having a distal portion, a proximal portion, and a lumen extending therebetween. The proximal portion is in communication with the distal end of the catheter. A suture extends through the catheter lumen and has a distal end and a proximal end. The distal end comprises a distal loop releasably attached to the plurality of circumferentially disposed struts at the distal portion of the cage. The suture has a frangible joint proximal of the distal loop and distal of the proximal end of the catheter. The system further includes a telescoping tissue grasper extending longitudinally through the catheter lumen. The telescoping tissue grasper comprises a shaft having a plurality of fingers circumferentially disposed at a distal end thereof. An expandable member can be disposed within the cage lumen or the cage can be self-expandable. The system further includes a retractable tissue grasper handle operably coupled to the proximal end of the catheter and in communication with the telescoping tissue grasper and a retractable suture handle operably coupled to the proximal end of the catheter and in communication with the proximal end of the suture.

BRIEF DESCRIPTION OF THE DRAWINGS

FIG. 16 is side view of a sheathed tissue grasper of a tissue ligation system in a constrained configuration according to an aspect of the present disclosure.

FIG. 17 is a side view of the tissue grasper of FIG. 16 in an expanded configuration according to an aspect of the present disclosure.

FIG. 18 is a side view of a tissue grasper of a tissue ligation system with an expandable member attached to the shaft of the tissue ligation system according to an aspect of the present disclosure.

DETAILED DESCRIPTION

The present disclosure relates to systems and methods of ligating tissue. As used herein with respect to a described element, the terms "a," "an," and "the" include at least one or more of the described elements including combinations thereof unless otherwise indicated. Further, the term "or" refers to "and/or" unless otherwise indicated. In addition, when an element is referred to as being "on," "attached" to, "connected" to, "coupled" with, "contacting," in "communication" with etc., another element, it can be directly on, attached to, connected to, coupled with, contacting, or in communication with the other element or intervening elements may also be present. In contrast, when an element is referred to as being, for example, "directly on," "directly attached" to, "directly connected" to, "directly coupled" with, "directly contacting," or in "direct communication" with another element, there are no intervening elements present. An element that is disposed "adjacent" to another element may have portions that overlap or underlie the adjacent element. Components of a tissue ligation system can be pre-assembled or require at least partial assembly before use. The tissue ligation system is in an assembled configuration when all of the components have been properly coupled or connected and the tissue ligation system is ready for use in a patient to ligate tissue. A "patient" refers to a mammal and is preferably a human being. All components of a tissue ligation system are used for medical purposes and are therefore sterile. As used herein a "catheter" excludes an endoscope.

Figure 1:
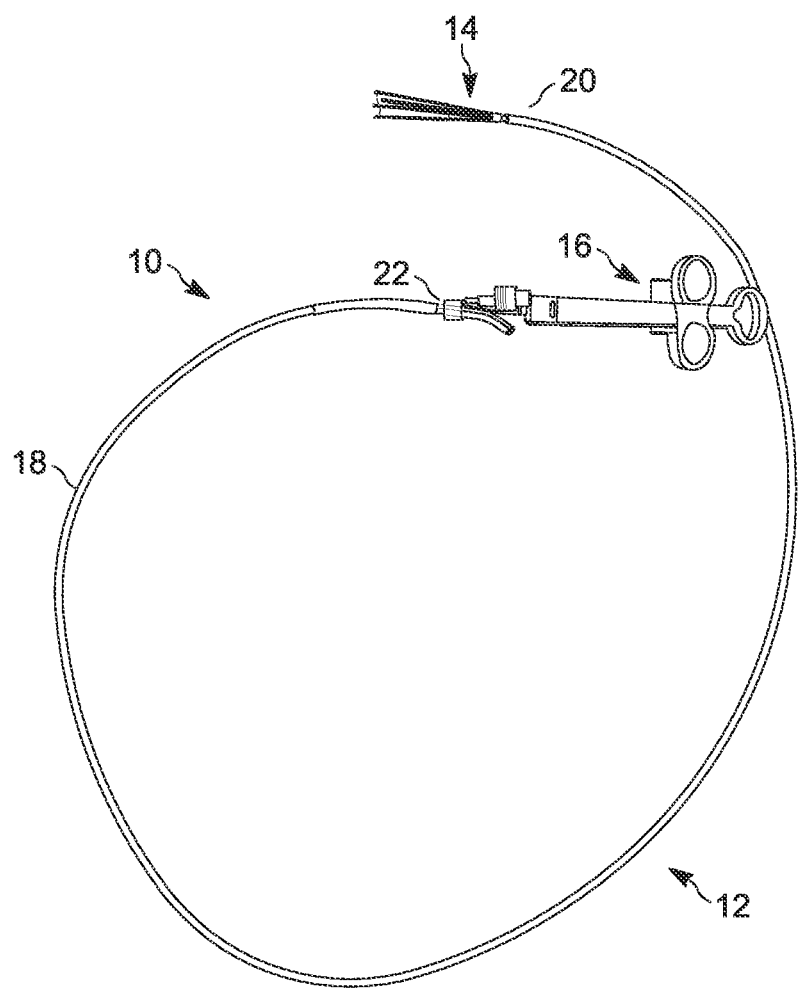
FIG. 1 is a top view of a tissue ligation system according to an aspect of the present disclosure.
Figure 2:
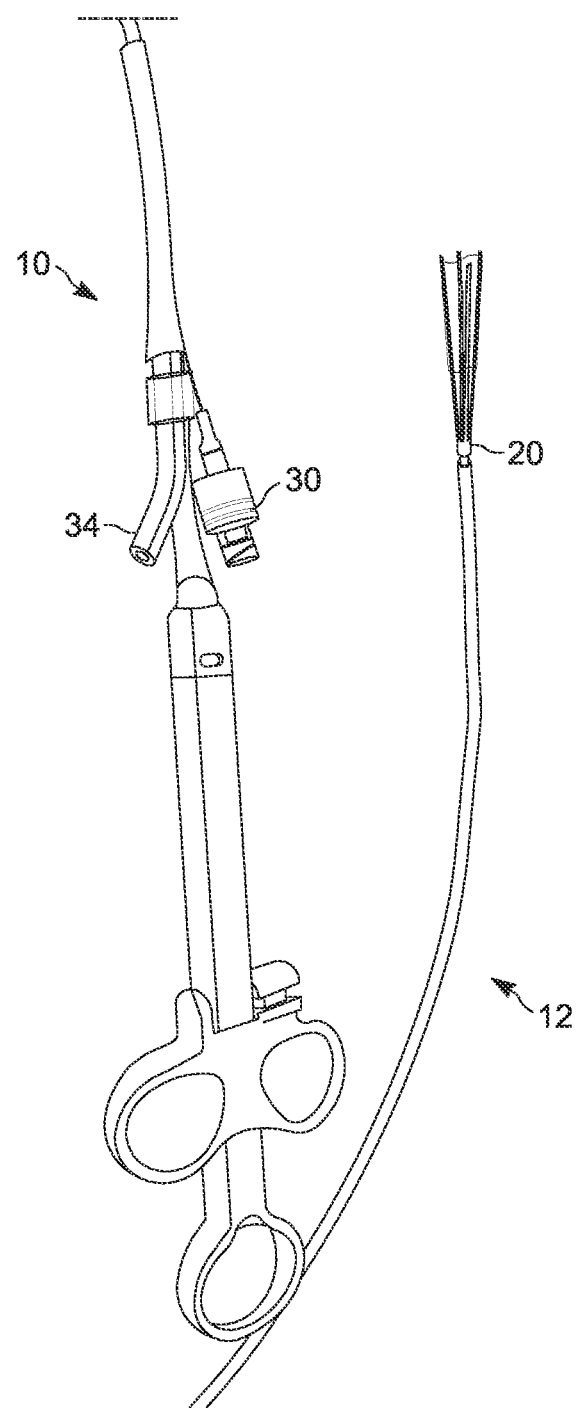
FIG. 2 is a top view of a tissue ligation system according to an aspect of the present disclosure.
Figure 3:
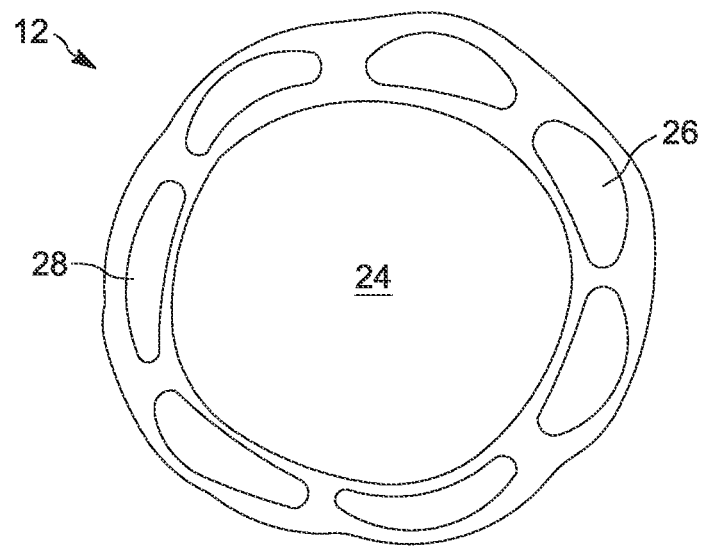
FIGS. 3 and 3A are cross-sectional views of multi-lumen catheters of a tissue ligation system according to an aspect of the present disclosure.
Figure 3A:
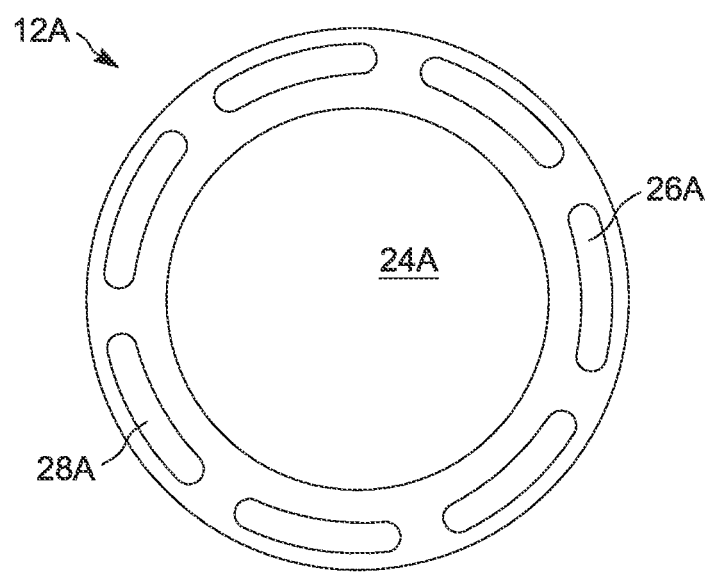

Referring to FIGS. 1 and 2, in an aspect, a tissue ligation system 10 comprises a multi-lumen catheter 12, a ligation apparatus 14, and a retractable handle 16. Catheter 12 has a distal end 20, a proximal end 22 and a catheter body 18 extending longitudinally therebetween. The catheter has an outer diameter smaller than the inner diameter of a biopsy channel of an endoscope. A standard endoscope has an inner diameter of between about 7.5 millimeters (mm) and 12.1 mm and the inner diameter of a standard biopsy channel is approximately 3.0 mm such as 2.8 mm. These are exemplary measurements as the purpose of this feature is that the catheter is sized to be just smaller than the biopsy channel of an endoscope in order for the catheter to pass through this channel. The multi-lumen catheter can have a plurality of lumens as illustrated in FIG. 3 that can be used for a number of different purposes, but at the least, the catheter has a vacuum lumen 24, an inflation lumen 26, and a suture lumen 28. In certain aspects, the vacuum lumen is a central lumen and the suture lumen and the inflation lumen are disposed about the vacuum lumen. FIG. 3A illustrates an exemplary configuration of the lumens of a multi-lumen catheter 12A. The ability of the tissue ligation system (such as vacuum at the expandable hood described below) to suction tissue is an important first step of ligating tissue. Due to the limits of the biopsy channel diameter of an endoscope, lumen arrangement and size of a multi-lumen catheter can be important to achieve the greatest amount of suction and the largest diameter size of the vacuum lumen necessary to properly and adequately suction tissue into the expandable hood of the tissue ligation system. For example, as depicted in FIG. 3A, smaller lumens, such as lumens 26A and 28A are oval shapes instead of circular shapes in order to leave as much space as possible for vacuum lumen 24A. Oval shape lumens can allow more easily for the suture and the wire to pass through a lumen as well. During wire insertion, an oval shape lumen can be expanded to a more circular shape temporarily to allow the wire to pass through the lumen easily. The lumen can then transition back to the original oval shape to leave space for the vacuum lumen.

Figure 4:
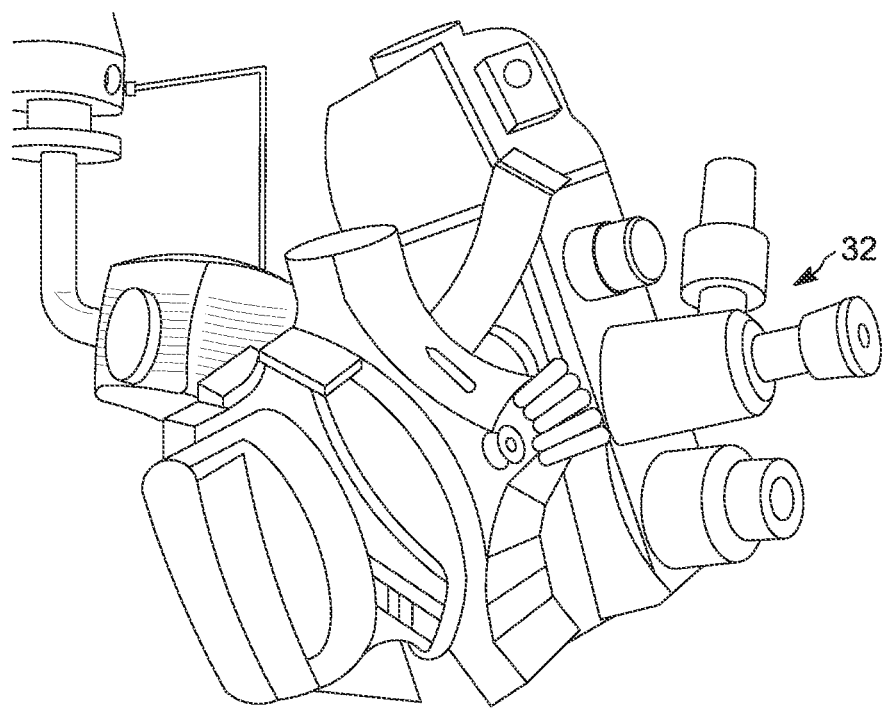
FIG. 4 is a perspective view of an adapter of a tissue ligation system attached to the control body of an endoscope according to an aspect of the present disclosure.

Vacuum lumen 24 can extend longitudinally through catheter body 18 and can have a proximal end in fluid communication with a vacuum port 30 in an assembled configuration. Preferably vacuum port 30 can be operably coupled to an adapter 32 depicted in FIG. 4, which, in turn, can be attached to the control body of an endoscope in an assembled configuration. As such, vacuum lumen 24 of catheter 12 can be in fluid communication with a suction lumen of an endoscope so that the endoscope delivers suction through vacuum lumen 24 of catheter 12. In this way, the catheter does not have to be directly attached to a separate vacuum source but rather can rely on the dedicated suction lumen of the endoscope to provide suction to the catheter. Alternatively, the vacuum lumen of the catheter can be in direct fluid communication with a suction source, such as a syringe, for example. The suction source can be any suitable device that can cause tissue to be suctioned into the hood of the ligation apparatus (described below). For example, the suction source can be a syringe or vacuum.

The inflation lumen of the catheter can be in direct fluid communication with an inflation source, such as a syringe, or small plastic or rubber bladder, for example. The inflation source can be, for example, an air, gas or fluid source. Suture lumen 28 of catheter 12 can extend longitudinally through catheter body 18 and can have an inner diameter sized to accommodate a suture.

Certain components of ligation apparatus 14 can be located at distal end 20 of catheter 12. For instance, referring to FIGS. 5-8, ligation apparatus 14 can include an expandable member 36 located at distal end 20 of catheter 12 and an expandable hood 38 disposed about expandable member 36 and also located at distal end 20 of catheter 12. Ligation apparatus 14 can also include suture 40 extending through the suture lumen of the catheter and having a proximal portion attached to a wire.

Figure 5:
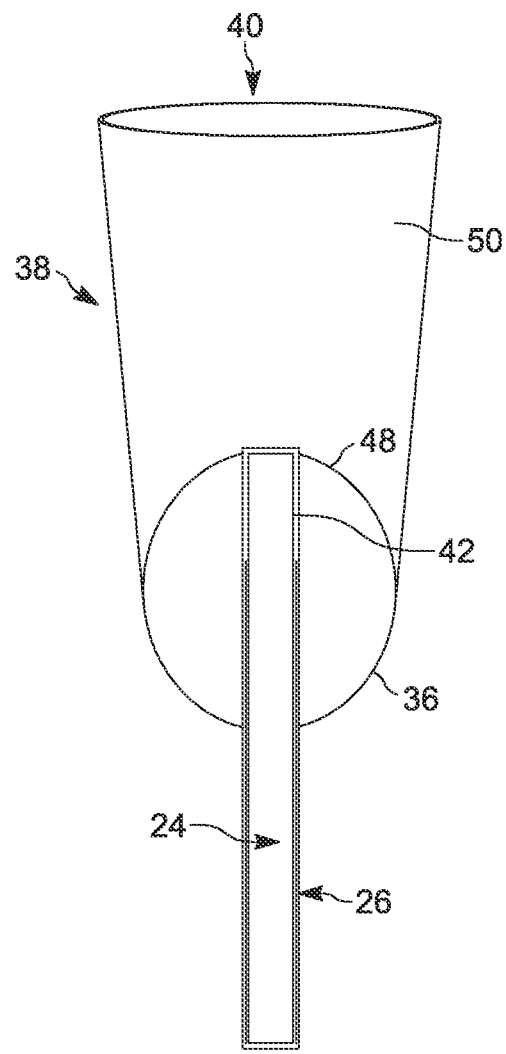
FIG. 5 is a schematic illustration of the distal portion of a multi-lumen catheter including a ligation apparatus according to an embodiment of the present disclosure.
Figure 6:
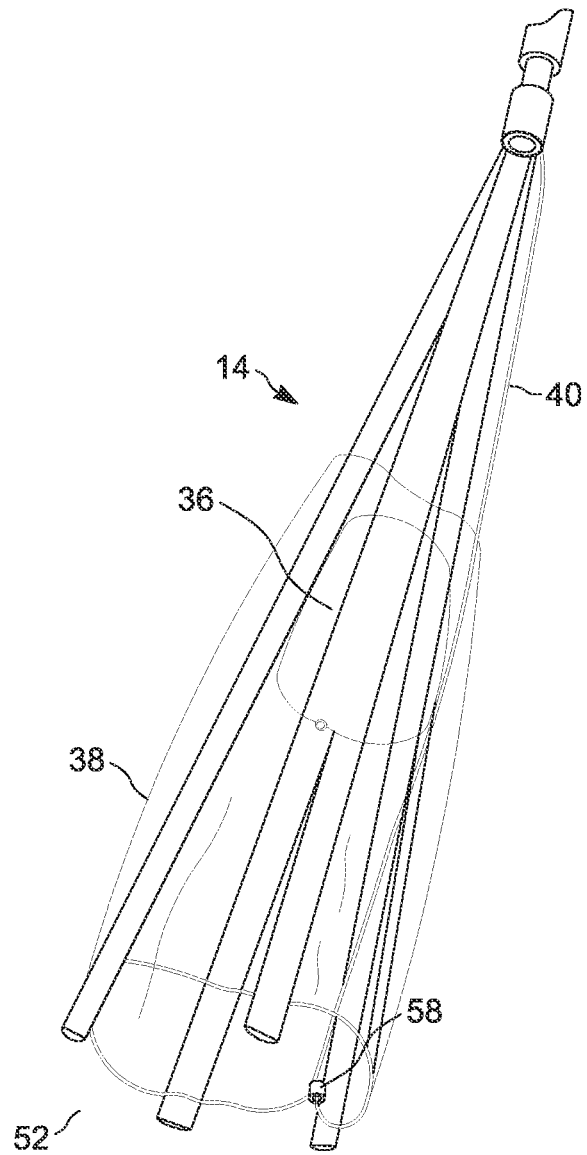
FIG. 6 is a side view of a ligation apparatus of a tissue ligation system according to an aspect of the present disclosure.
Figure 7:
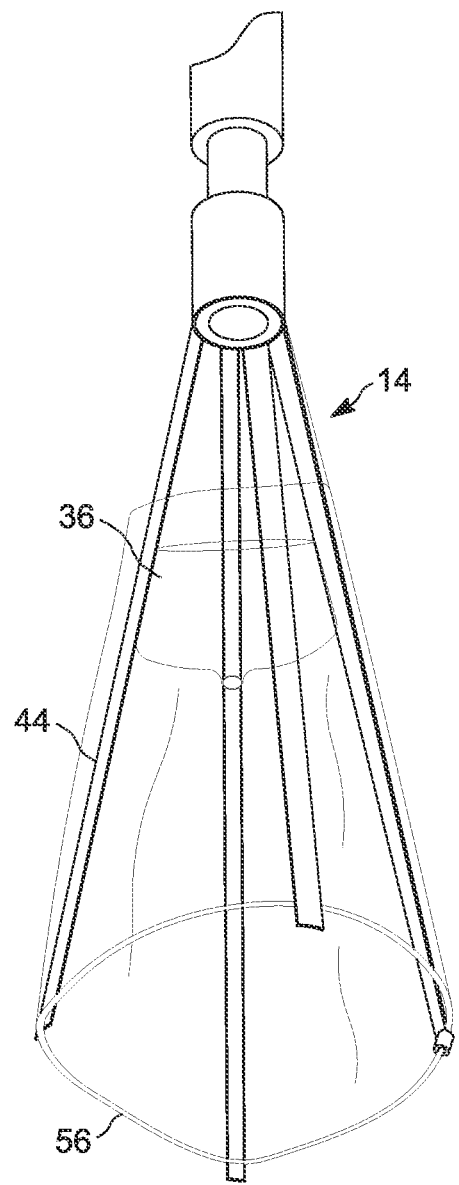
FIG. 7 is a side view of a ligation apparatus of a tissue ligation system according to an aspect of the present disclosure.
Figure 8:
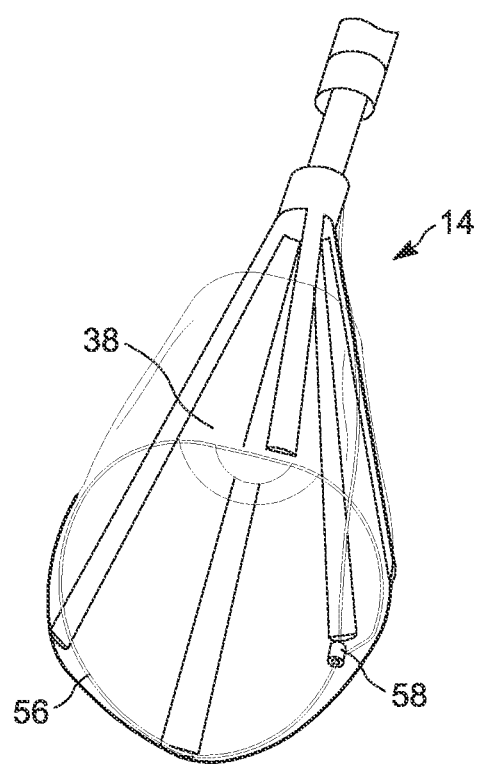
FIG. 8 is a top view of a ligation apparatus of a tissue ligation system according to an aspect of the present disclosure.
Figure 9:
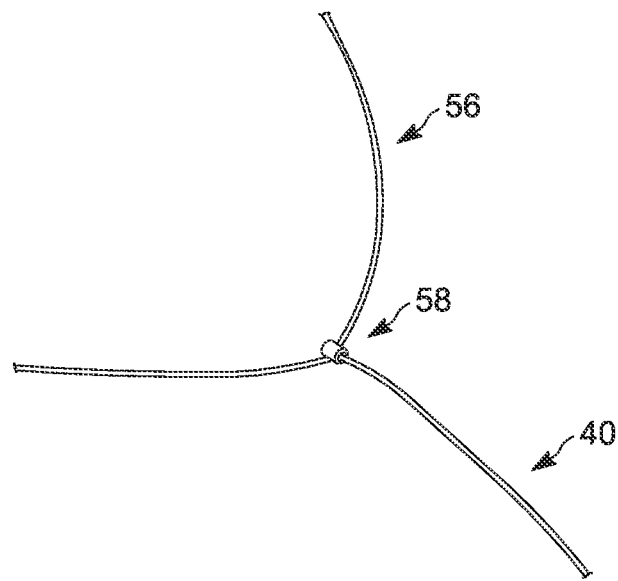
FIG. 9 is a side view of a suture, distal suture loop and collar of a ligation apparatus of a tissue ligation system according to an aspect of the present disclosure.

Expandable member 36 can have an interior opening 42 in fluid communication with inflation lumen 26 of catheter 12 as schematically illustrated in FIG. 5. The expandable member can be bonded to the outer surface of the catheter body. The expandable member can include any suitable device that is capable of expanding or de-compressing and contracting or compressing. For example, the expandable member can be an expandable balloon, a bladder, or an umbrella or parachute-like device. In the case of an expandable member that has a hollowed interior that accepts a material to inflate the expandable member, the expandable member can be inflated or diluted by delivering a fluid, air or other gas to the interior of the expandable member via the inflation lumen of the catheter body.

The expandable hood of the ligation apparatus can include a frame comprising a plurality of struts 44 disposed about the inner or outer surface of the expandable hood to provide patency to the hood when expanded. The expandable hood can have any suitable shape that allows tissue to be suctioned into a cavity (also referred to herein as a "suction cup") of the hood. For example, the expandable hood can be funnel-shaped. In certain embodiments, the hood is transparent.

In certain aspects, the ligation apparatus does not include an expandable member but rather the expandable hood is self-expanding. For example, the expandable hood can comprise a flexible material such as a flexible plastic membrane including, for example, polyurethane, a polyether block amide, etc. The expandable hood also can be fabricated from a shape memory alloy. As schematically depicted in FIG. 5, in an expanded configuration expandable hood 38 and the distal outer surface 48 of expandable member 36 can define a space that serves as a suction cup 50 (as described in more detail below).

Figure 10:
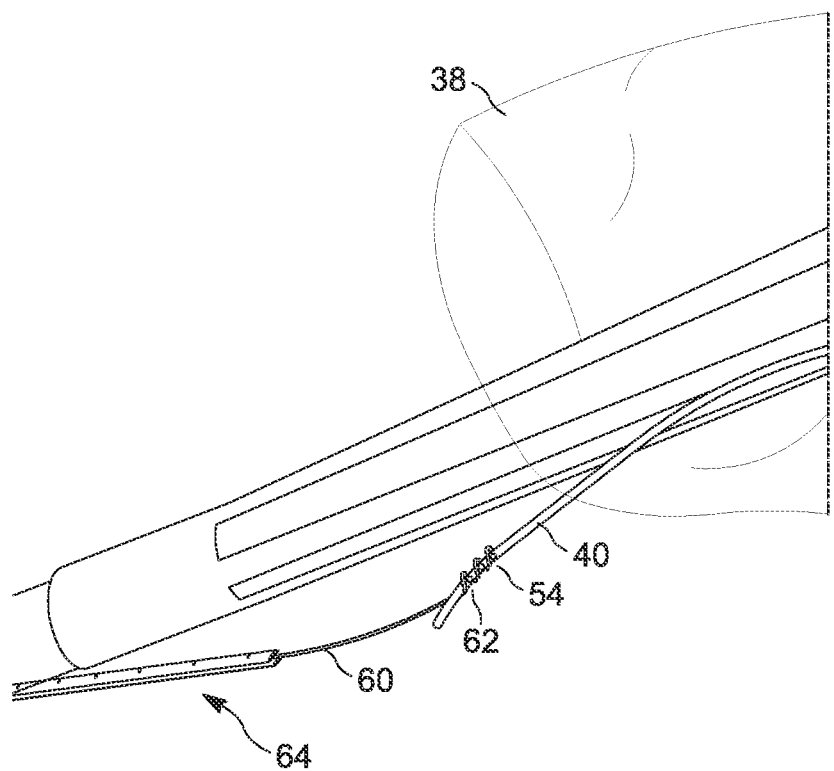
FIG. 10 is a side view of the distal portion of a tissue ligation system according to an aspect of the present disclosure.

As stated above, ligation apparatus 14 includes a suture 40. Suture 40 can have a distal portion 52 and a proximal portion 54 as collectively illustrated in FIGS. 6-10. Distal portion 52 comprises a distal loop 56 and a collar 58. Collar 58 permits movement of the suture in one direction and resists movement of the suture in the opposite direction. Collar 58 can have micro-engineered features that accomplish this such as inwardly bent teeth, for example, that allow the suture to move freely in one direction but grip the suture when the suture moves in an opposite direction. For instance, the collar can be a pall nut or a segment of a hypotube. The suture can be pre-loaded in the catheter. Referring to FIG. 10, proximal portion 54 of suture 40 is releasably coupled to a wire 60 (as described in more detail below).

Tissue ligation system 10 further includes a retractable handle 16 located at proximal end of catheter 12 and operably coupled to wire 60 in an assembled configuration.

Figure 11:
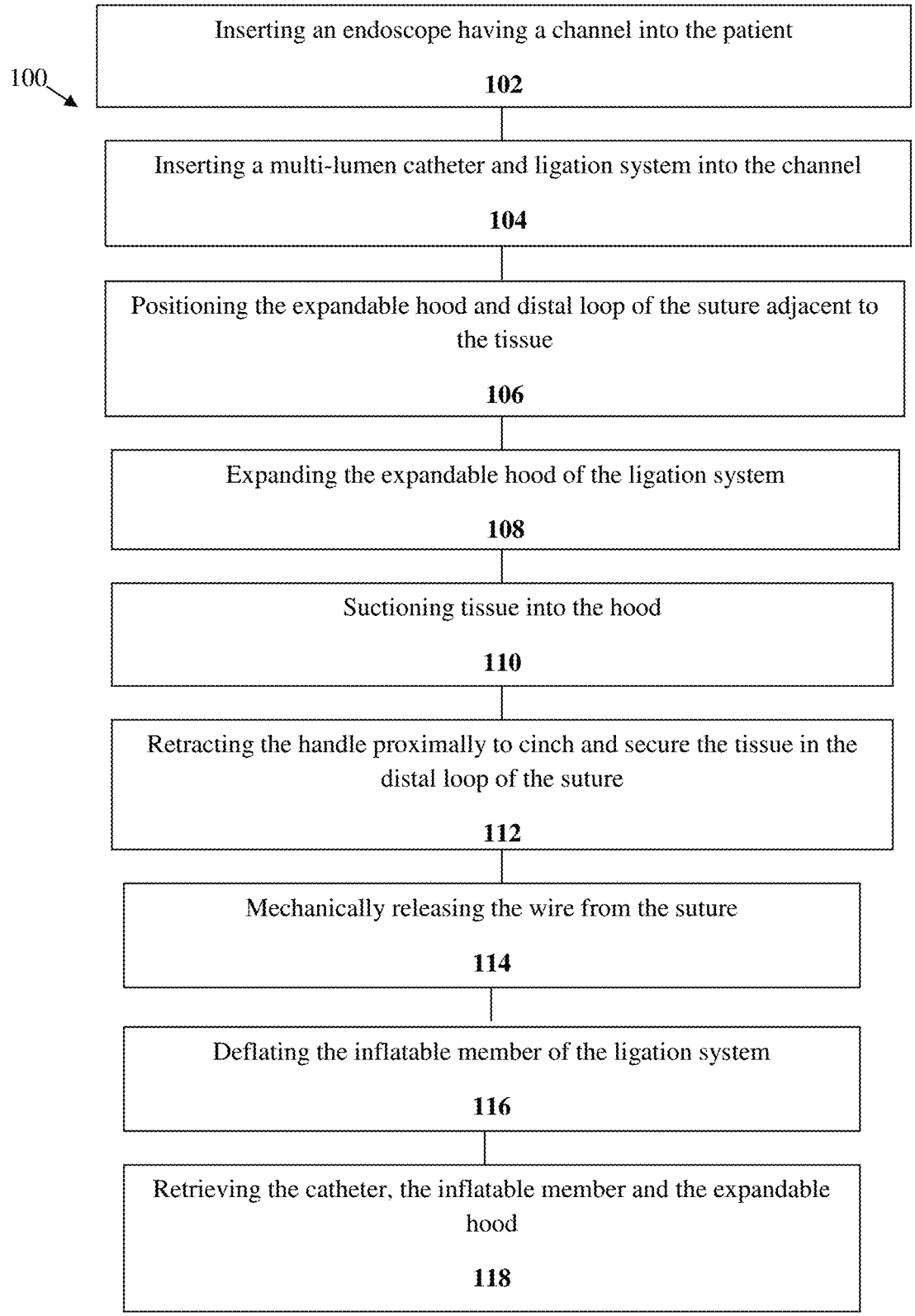
FIG. 11 is a flow chart outlining steps of a method of ligating tissue according to an aspect of the present disclosure.

Referring to FIG. 11, the present disclosure also provides methods for ligating tissue in a patient. Method 100 can comprise inserting an endoscope into a patient 102. An endoscope generally includes a water tube, an air tube, a biopsy/suction channel, fiberoptic light guides, and a fiberoptic image bundle. The method can further include inserting components of tissue ligation system into the biopsy/suction channel of the endoscope 104. Such components of the tissue ligation system can include a multi-lumen catheter and a ligation apparatus. The multi-lumen catheter can have a vacuum lumen, a suture lumen, and an inflation lumen. The ligation apparatus can include an expandable member located at the distal end of the multi-lumen catheter and an expandable hood disposed about the expandable member. The ligation apparatus can also include a suture extending through the suture lumen of the multi-lumen catheter. The suture can have a distal portion comprising a distal loop and a collar. The collar can permit movement of the suture in one direction and resist movement of the suture in an opposite direction. The suture can have a proximal portion releasably coupled to a wire.

After the tissue ligation system is inserted into the patient, the method can further include positioning distal components of the ligation apparatus adjacent to the tissue to be ligated 106. In particular, the expandable hood and the distal loop of the suture can be positioned adjacent to the tissue to be ligated. The method can then comprise inflating the inflatable member to expand the expandable hood 108 and suctioning the tissue into the suction cup defined by the distal portion of the expandable member and the expandable hood 110. The method can further comprise retracting the handle proximally to reduce the size of the distal suture loop so that the suture loop engages the tissue, cinches the tissue and "locks" the tissue into the distal suture loop in effectively a single substantially continuous step 112. Although multiple sutures can be employed to ligate tissue, for any given suture, the given suture both cinches and secures or "locks" the tissue into the distal loop. Because the collar permits movement of the suture in one direction and resists movement of the suture in the opposite direction, when the suture is pulled proximally, the collar prevents any further movement of the suture once the suture has cinched the tissue. As such, the size of the suture distal loop stays the same and there is no need for any further suture or part of the suture to be manipulated to lock or secure the tissue in place in the suture loop.

After the tissue has been ligated and strangulated, the suture can be severed. For example, method 100 can then comprise mechanically releasing the wire from the suture 114. The method can further comprise deflating the inflatable member 116 and retrieving the catheter, the inflatable member and the expandable hood 118. The suture and the collar can be the only components of the ligation apparatus that remain inside the patient.

The wire can be mechanically released from the suture in a number of different ways. For example, the distal portion 62 of wire 60 can be wound around the proximal portion 54 of suture 40 as depicted in FIG. 10. The handle of the tissue ligation system can be retracted proximally to apply a pulling force on the wire to separate the wire from the suture. FIG. 10 depicts a hypotube 64 that can be used to separate the wire from the suture. In such an embodiment, the wire is thinner than the suture so that the suture cannot fit within the lumen of the hypotube but rather just the wire can enter the lumen and can be cut from the suture. Other devices can also be used to cut the wire from the suture and a hypotube is only exemplary. Further, a hypotube or other cutting device is not necessary as long as the pulling force applied to the wire is greater than then breaking strength of the wire. Alternatively, a crimp or other releasable mechanical fastener can be used to releasably couple the distal portion of the wire with proximal portion of the suture Although the above methods describe mechanical ways to separate the suture from the wire, other methods can be used such as the application of heat or a chemical agent to uncouple the wire from the suture.

Figure 12:
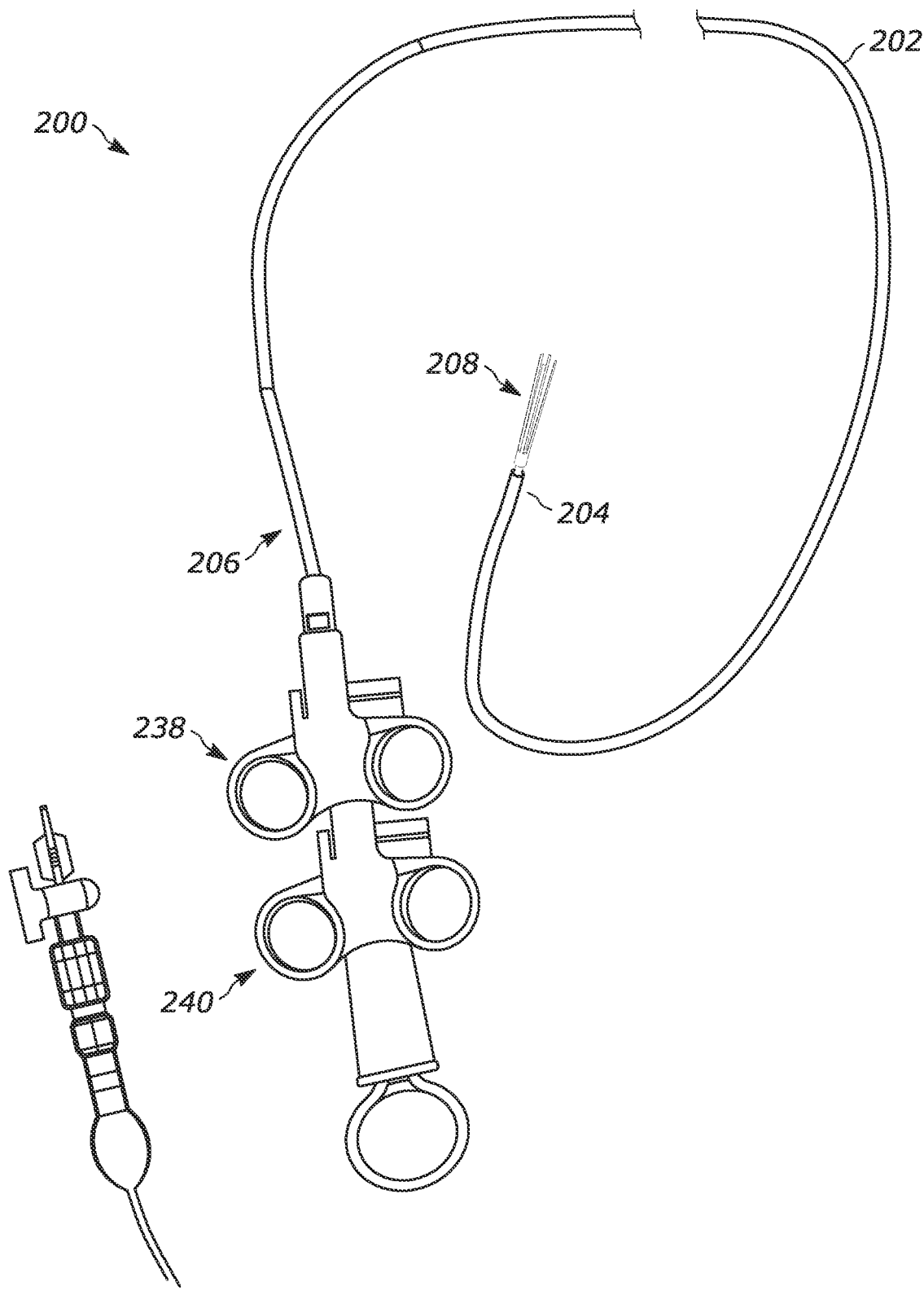
FIG. 12 is a top view of a tissue ligation system according to an aspect of the present disclosure.
Figure 13:
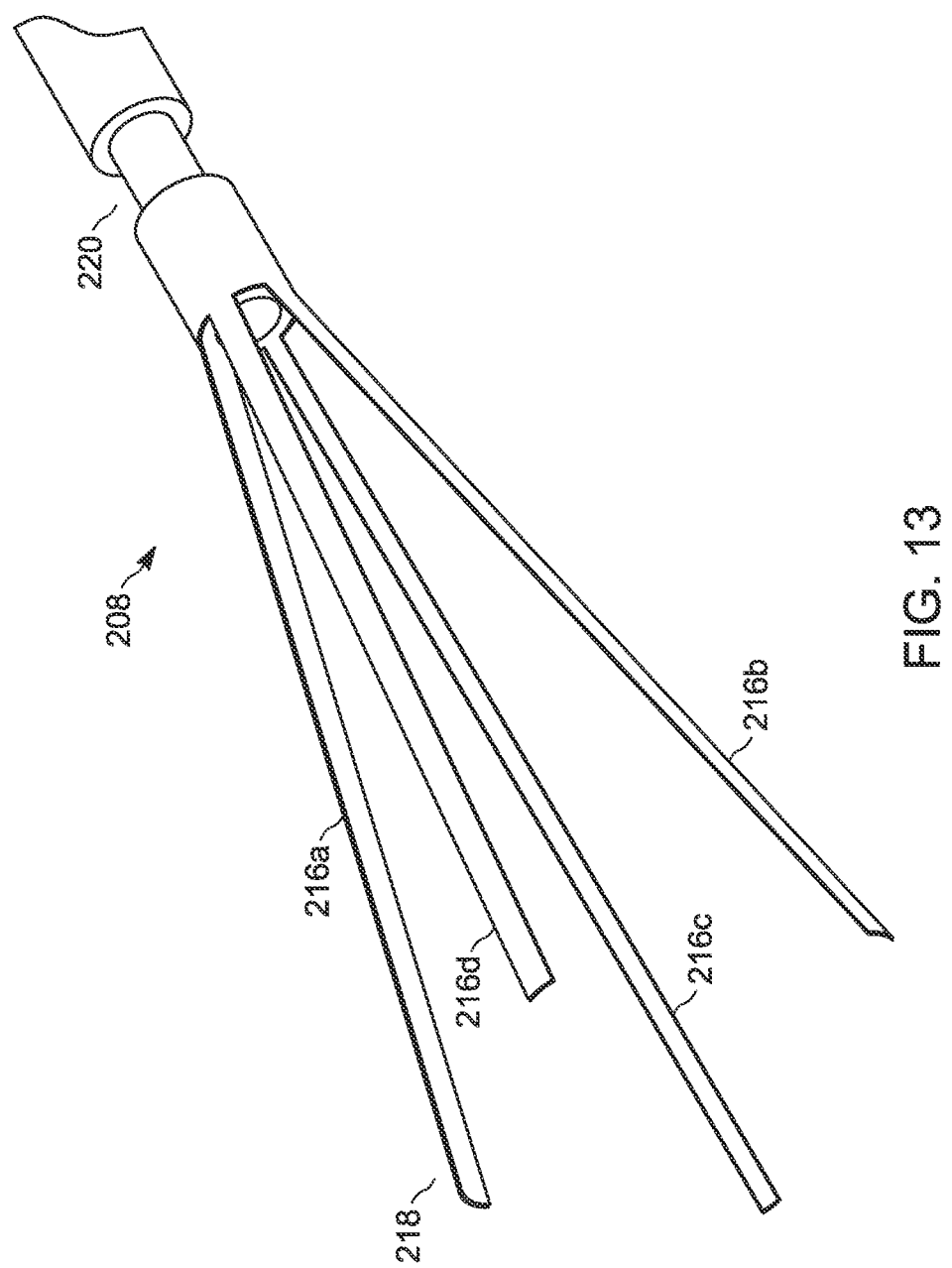
FIG. 13 is a top view of the cage of the tissue ligation system depicted in FIG. 12 according to an aspect of the present disclosure.
Figure 14:
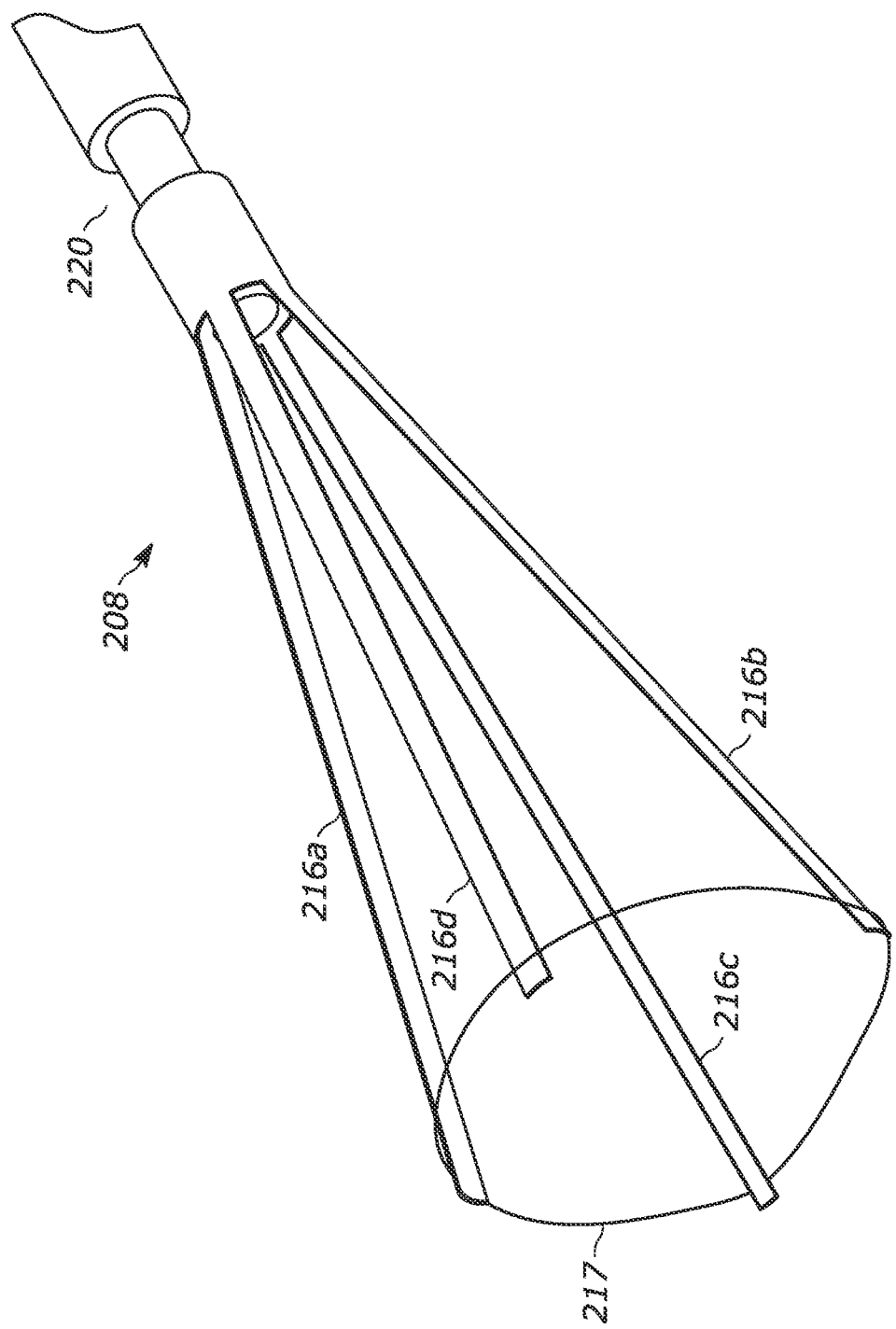
FIG. 14 is a perspective view of the cage of FIG. 13 depicting a thread attached to the plurality of struts of the cage according to an aspect of the present disclosure.
Figure 19:
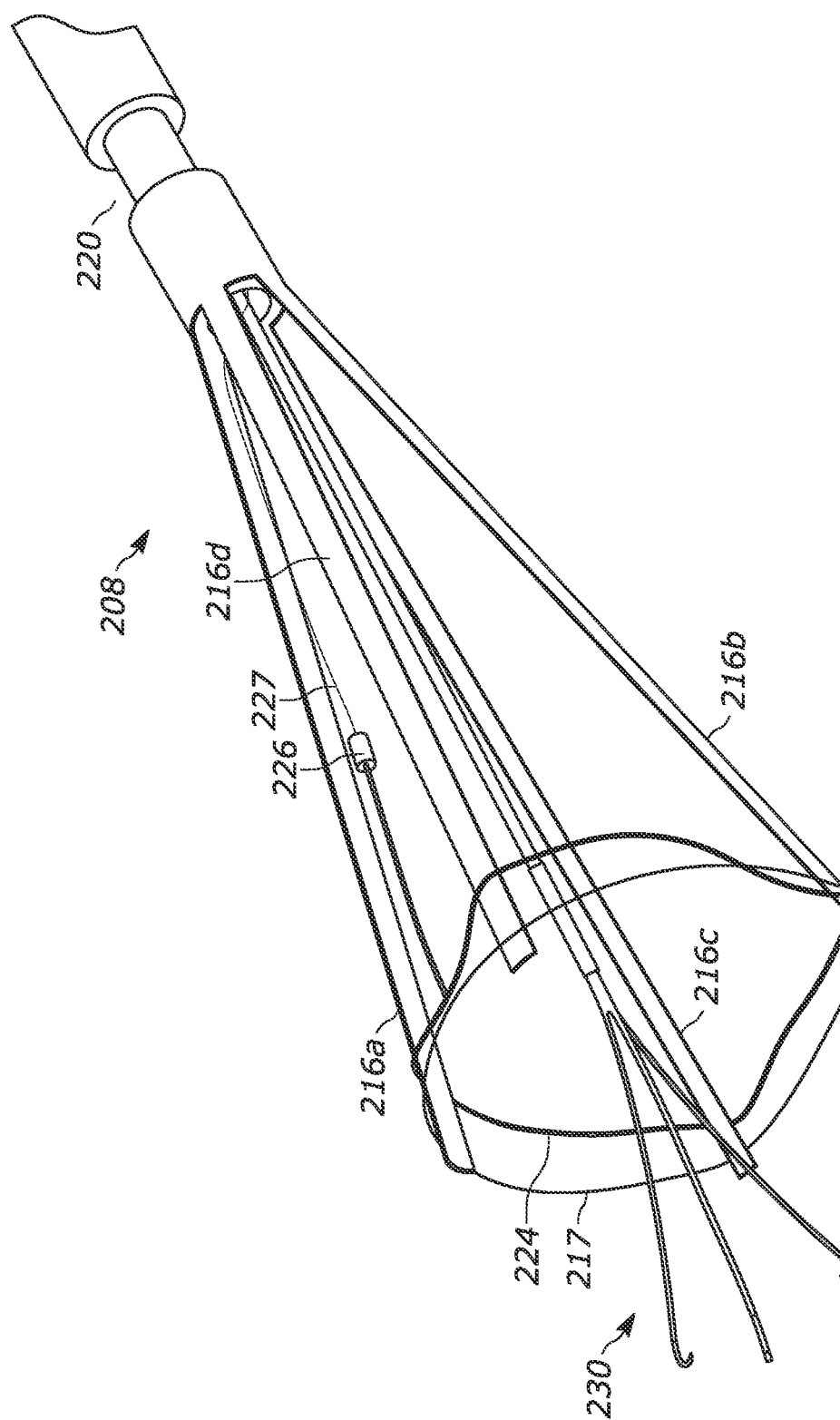
FIG. 19 depicts the distal portion of tissue ligation system according to an aspect of the present disclosure.

Referring to FIG. 12, in an embodiment, a tissue ligation system 200 can comprises a catheter 202 having a distal end 204, a proximal end 206 and a lumen extending longitudinally therethrough. The catheter has an outer diameter smaller than the inner diameter of a biopsy channel of an endoscope. Referring to FIG. 13, a cage 208 can be disposed at the distal end of the catheter and can comprise a plurality of circumferentially disposed struts 216. Cage 208 can have a distal portion 218, a proximal portion 220, and a lumen 222 extending therebetween. The proximal portion can be in communication with the distal end of the catheter. The cage can be self-expandable or can be expanded by a separate expandable member as described below. Referring to FIGS. 14 and 19, a thread 217 can be circumferentially attached to the plurality of struts 216 configured to mitigate bending of the plurality of struts 216 during ligation.

Figure 15:
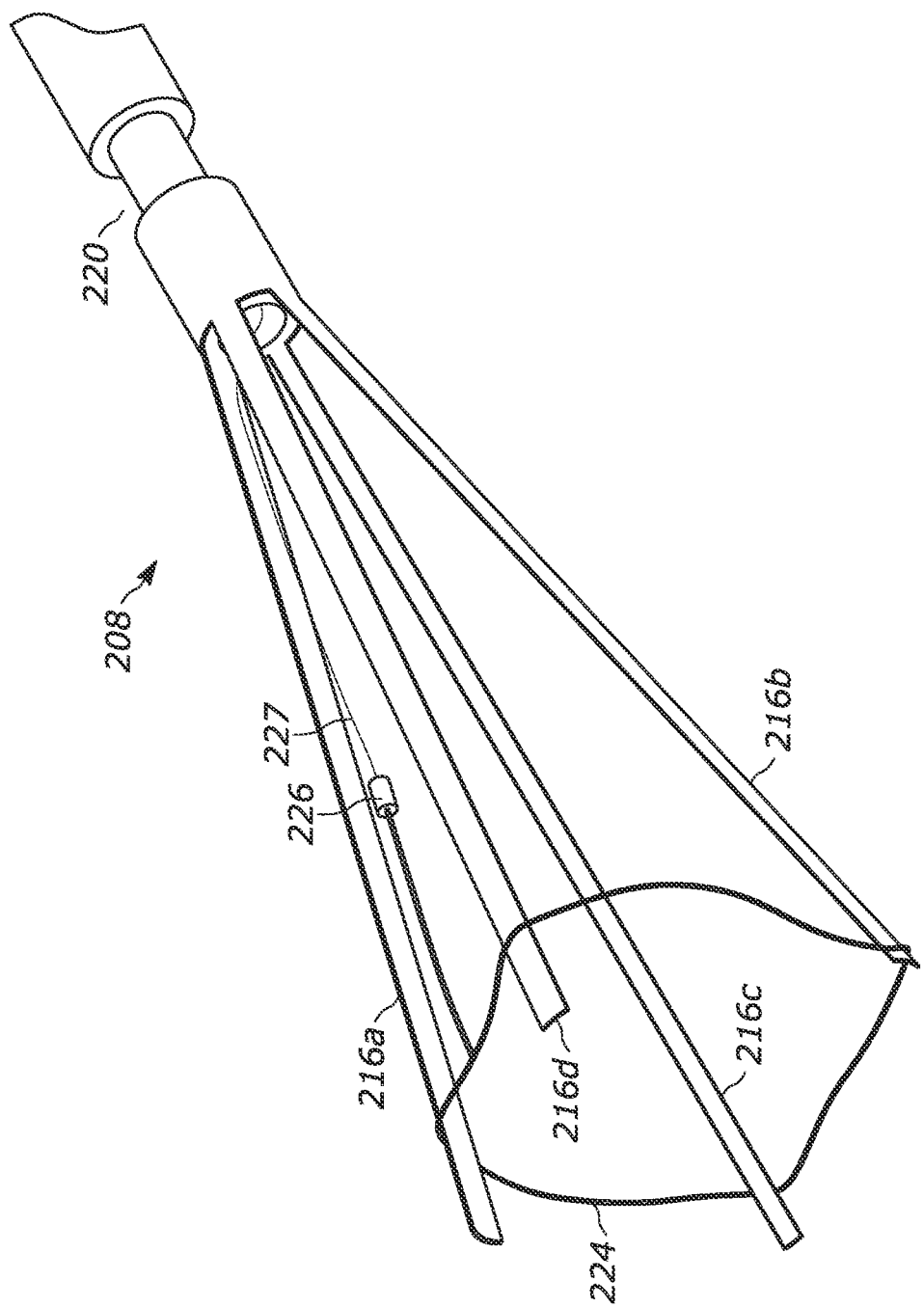
FIG. 15 is a perspective view of the cage of FIG. 13 depicting a suture and suture loop disposed on the distal end of the plurality of struts of the cage and having a proximal end attached to a thread at a frangible joint according to an aspect of the present disclosure.

Referring to FIG. 15, a suture 224 can extend through the catheter lumen and can have a distal end and a proximal end. The distal end can comprise a distal loop 228 releasably disposed on the plurality of circumferentially disposed struts 216 at the distal portion of cage 208. As illustrated in FIG. 15, suture 224 can have a frangible joint 226 proximal of distal loop 228 and distal of proximal end 206 of catheter 202. The force necessary to break joint 226 is less than the force necessary to break distal loop 228. Further, the force necessary to break distal loop 228 is greater than the force necessary to break the suture at joint 226 and, preferably, the portion of suture or a thread attached to the suture proximal of joint 226 thereby preventing premature detachment of the suture at suture joint 226. As shown in FIG. 15, in certain embodiments, the proximal end of the suture is tied to the distal end of a thread 227. The tensile strength of the suture is greater than the tensile strength of the thread so that the suture can break from the thread at the frangible joint after the suture loop has been deployed to ligate tissue and the catheter is withdrawn from the patient. For example, if the strength of the suture is defined by how many pounds of pulling force the suture can hold until it breaks, the strength of the suture is greater than the strength of the thread. For example, if the suture can hold up to twelve pounds of pulling force, the thread can hold up to eight pounds of pulling force. The frangible joint is the weak point of the suture connected to the thread, which is the break point after the tissue ligation is completed. Preferably the joint break force is no more than six pounds to make sure it provides enough force for ligation, while still being able to break away from the desired point.

As described above, a collar can be disposed about the suture permitting movement of the suture in one direction and resisting movement in an opposite direction.

Referring to FIGS. 16 and 17, the issue ligation system can further include telescoping tissue grasper 230 extending longitudinally through the lumen of catheter 202. Telescoping tissue grasper 230 can have a shaft 232 having a plurality of fingers 234 circumferentially disposed at a distal end thereof. It's comprised of a sheath and a metal wire with three prongs at the distal end. At the distal end of each prong, there is a hook about 120 degree bending. The way the tissue grasper works is: step 1, the metal wire is pushed out of the sheath. The prongs automatically open to engage the tissue; step 2, the metal is pulled back into the sheath while maintaining engagement with the tissue; step 3, three prongs will close towards each other, until they are stopped because of the tissue and the sheath working together. The tissue is fully grabbed at this point. To release the tissue, the metal wire is pushed out of the sheath. The three prongs will open automatically.

Referring to FIG. 18, a tissue ligation system can also include an expandable member 236 disposed within the lumen of cage 208. In certain aspects, the expandable member is disposed on shaft 232 of the tissue grasper 230 proximal of the plurality of fingers 234 as depicted in FIG. 18. As with embodiments above, the expandable member can be, for example, a balloon, a bladder, or an umbrella or parachute-like device. The tissue ligation system can further include an inflation source configured to be operably coupled to the proximal end of the catheter to inflate/expand the expandable member. For example, the catheter can include an inflation lumen that is configured to be in fluid communication with an inflation source, such as a syringe, or small plastic or rubber bladder, for example. The inflation source be used to deliver, for example, air, gas or fluid to the expandable member.

Referring back to FIG. 12, a retractable tissue grasper handle 240 can be operably coupled to the proximal end of catheter 202 and in communication with the telescoping tissue grasper 230 and a retractable suture handle 238 also can be operably coupled to the proximal end of catheter 202 and in communication with the proximal end of suture 224.

Figure 20:
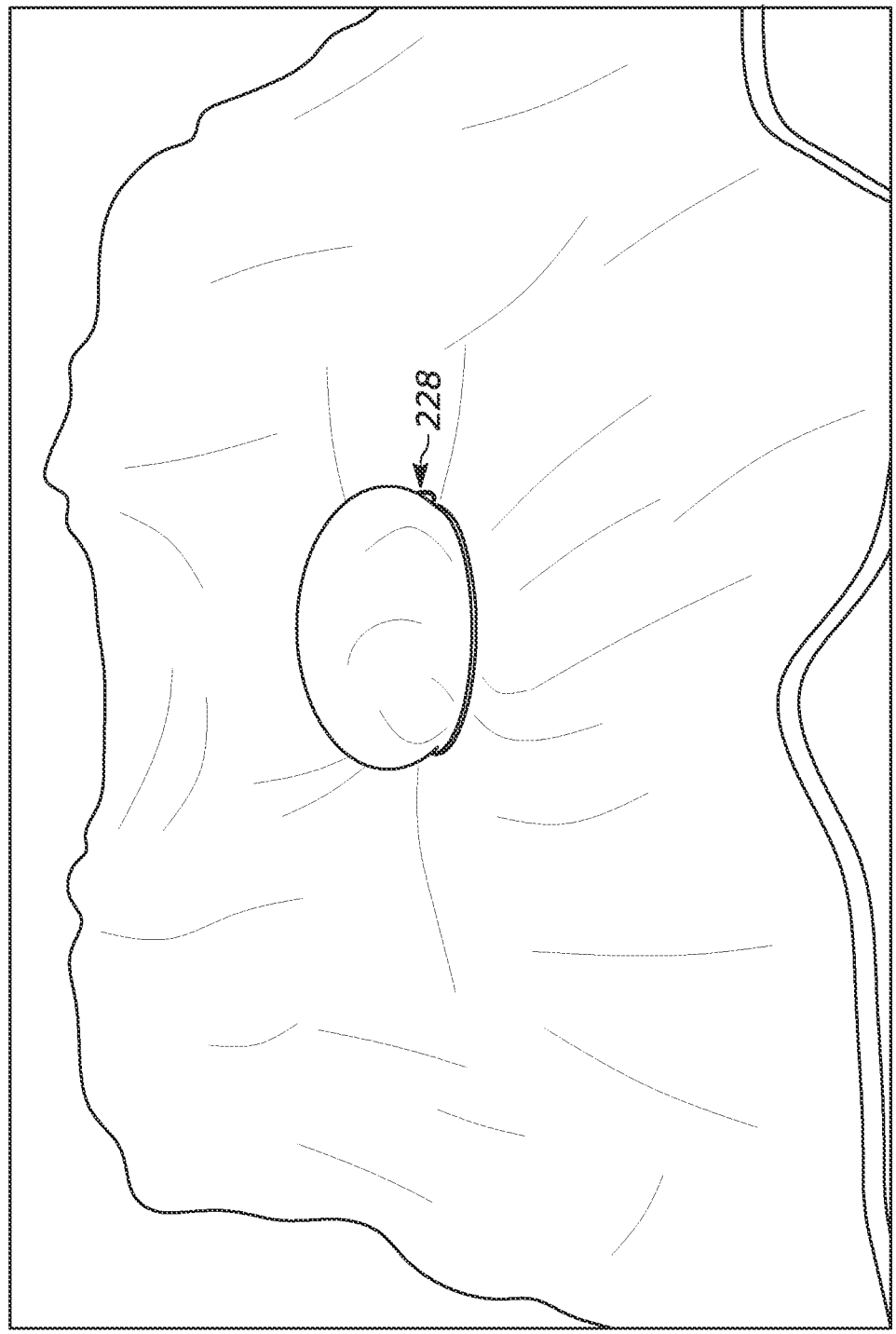
FIG. 20 is a schematic illustration of a distal loop of a suture of a tissue ligation system cinched around a material substituting as tissue according to an aspect of the present disclosure.
Figure 21:
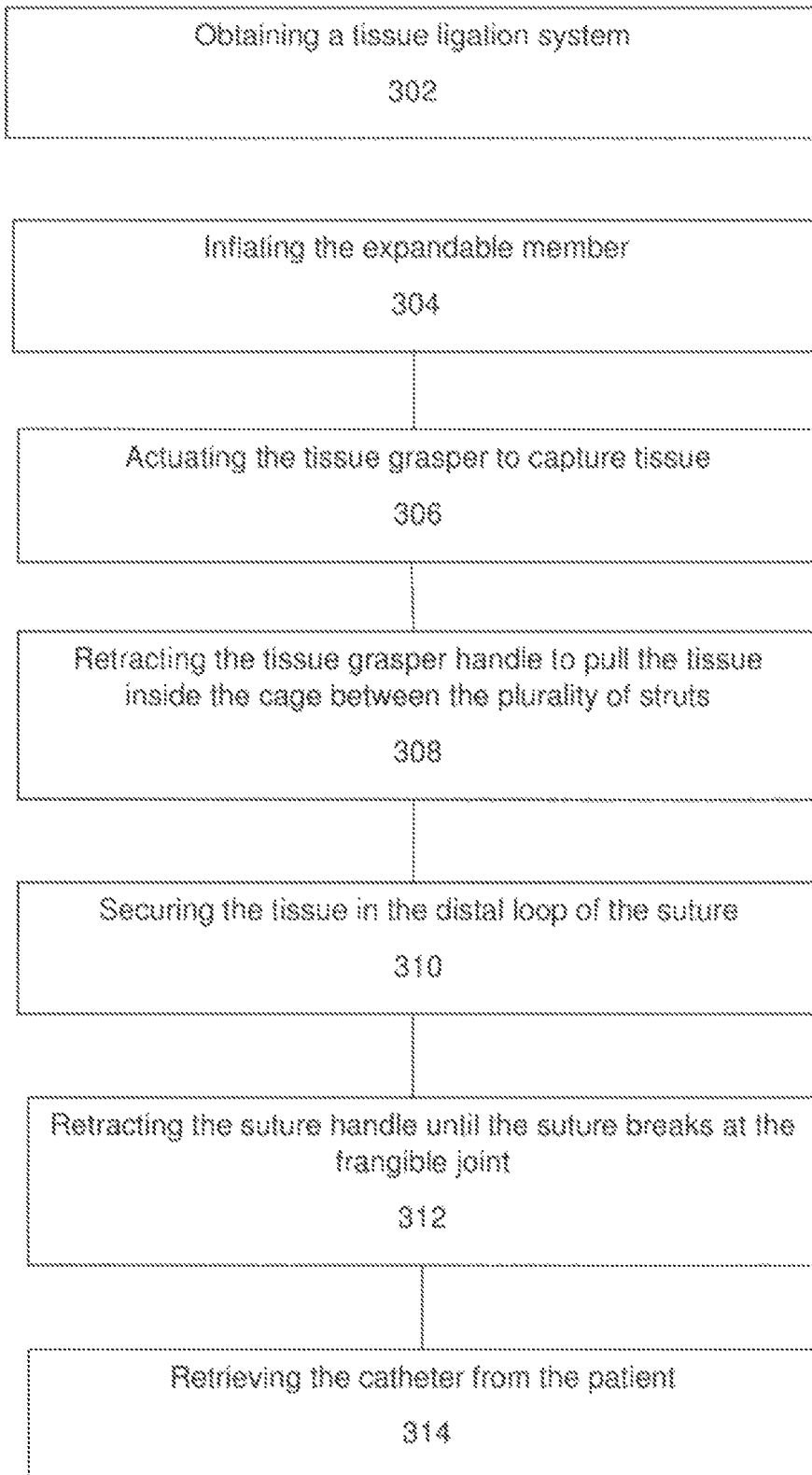
FIG. 21 is a flow chart outlining steps of a method of ligating tissue according to an aspect of the present disclosure.

In aspects where the tissue ligation system includes an expandable member and with reference to FIG. 21 a method of ligating tissue can involve obtaining a tissue ligation system 300, inflating the expandable member 302, actuating the tissue grasper to capture tissue 304, retracting the tissue grasper handle to pull the tissue inside the cage between the plurality of struts 306, securing the tissue in the distal loop of the suture 308, retracting the suture handle until the suture breaks at the frangible joint 310 and retrieving the catheter from the patient 312. In particular, in embodiments where an expandable member, such as a balloon, is attached to the shaft of the tissue grasper, the tissue grasper first can be positioned at the distal portion of the cage with the plurality of fingers in a closed position. The tissue grasper can then be actuated such that the plurality of fingers assumes an open position and grips the desired tissue to be ligated. The balloon can then be inflated. The tissue grasper can be retracted to pull the tissue back towards the cage with the plurality of fingers in a closed position. The expandable member is still positioned at the distal portion of the cage at this stage. As the tissue grasper is retracted further, the balloon is pulled back into the cage along with the captured tissue. As a result, the cage opens wider and wider to provide enough space for the tissue in the lumen of the cage. Once the expandable member is at a desired location, the retractable suture handle of the tissue ligation system can be locked to ensure the captured tissue remains inside the cage. The suture handle can be pulled back until the suture breaks at the frangible joint thereby cinching and ligating the captured tissue as illustrated in FIG. 20.

Methods as disclosed herein can be used in conjunction with the administration of pharmaceutical or biological agents. For example, methods of treating varices can include administering pharmaceutical agents, such as beta blockers, or biological agents as adjunct therapy.

Methods and devices as described herein can be used to ligate abnormal or otherwise undesirable tissue. Such tissue can include a varix in a vein, artery or lymphatic vessel. Non-limiting examples include esophageal varices and gastric varices. Such varices are dilated blood vessels in the esophagus or stomach generally caused by portal hypertension and commonly stemming from cirrhosis of the liver. Methods and devices can also be used to ligate a hemorrhoid; a polyp; a cancerous lesion that can be removed, for example, by endoscopic mucosal resection; an arteriovenous malformation; a Mallory-Weiss tear; a Dieulofoy's lesion; a multifocal venous malformations resulting in, for example, blue rubber bleb nevus syndrome; or diverticula resulting in, for example, diverticular bleeding. Accordingly, methods and devices as disclosed herein can be used to treat esophageal variceal bleeding, prevent primary variceal bleeding in patients with varices, prevent re-bleeding after an initial variceal hemorrhage, and treat rectal hemorrhoids.

Methods and systems as disclosed herein have several advantages, exemplary ones of which are described below. The catheter of the tissue ligation device has an outer diameter smaller than the inner diameter of a standard endoscope. As such, the tissue ligation system can provide a "through the scope" technique precluding the need for a second intubation needed for current tissue banding devices. This feature can also shorten the procedure time and the sedation/anesthesia time since the procedure can be done in one step with a single esophageal intubation, for example. The tissue ligation system does not add to the existing outer diameter of standard endoscopes since no cap attachment (into which tissue is suctioned) is needed as with current devices. As such, children or small adults with limited oropharyngeal space can be intubated since there is no banding cap needed that increases the endoscope diameter. Further, the tissue ligation system can provide a clinician with the ability to perform suctioning of the tissue away from the bodily lumen into which the tissue ligation device is inserted. For instance, a clinician can perform suctioning of a varix away from the wall of the esophagus thereby avoiding deep ulcerations often occurring in endoscopic sclerotherapy. In addition, the tissue ligation system can provide mechanical strangulation of tissue, such as a varix or mucosa, as opposed to injecting chemical agents such as sclerosing agents or adhesives into the bloodstream via the varix or the surrounding tissue thereby avoiding potential complications. A tissue ligation system as disclosed herein can also provide an improved field of vision during the endoscopic procedure compared to existing band ligation devices where visibility is significantly limited due to the cylindrical cap that is needed and that is attached to the leading end of the endoscope.

Each of the disclosed aspects and embodiments of the present disclosure may be considered individually or in combination with other aspects, embodiments, and variations of the disclosure. Further, while certain features of embodiments of the present disclosure may be shown in only certain figures, such features can be incorporated into other embodiments shown in other figures while remaining within the scope of the present disclosure. In addition, unless otherwise specified, none of the steps of the methods of the present disclosure are confined to any particular order of performance. Furthermore, all references cited herein are incorporated by reference in their entirety.

The invention claimed is:

1. A tissue ligation system comprising:
   a catheter having a distal end, a proximal end, and a lumen extending longitudinally therethrough, the catheter having an outer diameter smaller than an inner diameter of a biopsy channel of an endoscope;
   a cage comprising a plurality of circumferentially disposed struts and having a distal portion, a proximal portion, and a lumen extending therebetween, the proximal portion in communication with the distal end of the catheter;
   a suture extending through the catheter lumen and having a distal end and a proximal end, the distal end comprising a distal suture loop releasably disposed on the plurality of circumferentially disposed struts at the distal portion of the cage,
   a thread having a distal end tied to the proximal end of the suture at a frangible joint, the frangible joint proximal of the distal suture loop and distal of the proximal end of the catheter, wherein the force necessary to break the distal suture loop is greater than the force necessary to break the suture from the thread at the frangible joint; and
   a telescoping tissue grasper extending longitudinally through the catheter lumen, the telescoping tissue grasper comprising a shaft having a plurality of fingers circumferentially disposed at a distal end thereof.

2. The tissue ligation system of claim 1, further comprising an expandable member disposed within the cage lumen.

3. The tissue ligation system of claim 2, wherein the expandable member is located on the shaft of the tissue grasper proximal of the plurality of fingers.

4. The tissue ligation system of claim 1, wherein the cage is a self-expandable cage.

5. The tissue ligation system of claim 1, further comprising another thread circumferentially attached to the plurality of struts of the cage configured to mitigate bending of the plurality of struts during ligation.

6. The tissue ligation system of claim 1, further comprising a collar disposed about the suture, the collar permitting movement of the suture in one direction and resisting movement of the suture in an opposite direction.

7. The tissue ligation system of claim 1, further comprising an inflation source configured to be operably coupled to the proximal end of the catheter.

8. The tissue ligation system of claim 1, further comprising a sheath having a longitudinally extending sheath lumen through, the tissue grasper slidably disposed within the sheath lumen to transition the tissued grasper from a radially constrained configuration to a radially expanded configuration.

9. A method of ligating tissue comprising:
   obtaining the tissue ligation system of claim 1;
   actuating the tissue grasper to capture tissue;
   retracting the tissue grasper to pull the tissue inside the cage between the plurality of struts;
   securing the tissue in the distal suture loop of the suture;
   retracting the suture until the suture breaks at the frangible joint; and
   retrieving the catheter from the patient.

10. The method of claim 9, wherein the tissue is a varix, a hemorrhoid, a polyp, a cancerous lesion, an arteriovenous malformation, a Mallory-Weiss tear, a Dieulofoy's lesion, multifocal venous malformations resulting in blue rubber bleb nevus syndrome, diverticula, a combination thereof.

11. The system of claim 1, wherein the strength of the suture is greater than the strength of the thread.

12. The system of claim 11, wherein the tensile strength of the suture is greater than the tensile strength of the thread.

* * * * *